(12) United States Patent
Pantazis et al.

(10) Patent No.: US 9,476,830 B2
(45) Date of Patent: *Oct. 25, 2016

(54) SECOND HARMONIC IMAGING NANOPROBES AND TECHNIQUES FOR USE THEREOF

(75) Inventors: Periklis Pantazis, Pasadena, CA (US); Ye Pu, Pasadena, CA (US); Demetri Psaltis, St-Sulpice (CH); John H. Hong, Pasadena, CA (US); Scott E. Fraser, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1531 days.

This patent is subject to a terminal disclaimer.

(21) Appl. No.: 11/944,264

(22) Filed: Nov. 21, 2007

(65) Prior Publication Data

US 2012/0141981 A1 Jun. 7, 2012

Related U.S. Application Data

(60) Provisional application No. 60/860,439, filed on Nov. 21, 2006, provisional application No. 60/936,043, filed on Jun. 18, 2007.

(51) Int. Cl.
| | |
|---|---|
| *B82Y 15/00* | (2011.01) |
| *G01N 21/63* | (2006.01) |
| *B82Y 20/00* | (2011.01) |
| *G02F 1/37* | (2006.01) |

(52) U.S. Cl.
CPC ............ *G01N 21/636* (2013.01); *B82Y 15/00* (2013.01); *B82Y 20/00* (2013.01); *G02F 1/37* (2013.01)

(58) Field of Classification Search
None
See application file for complete search history.

(56) References Cited

U.S. PATENT DOCUMENTS

| 5,538,898 A | 7/1996 | Wickramasinghe et al. |
| 5,952,180 A | 9/1999 | Ju |
| 6,624,915 B1 | 9/2003 | Kirkpatrick et al. |

(Continued)

FOREIGN PATENT DOCUMENTS

| WO | 2004106896 A2 | 12/2004 |
| WO | 2008140584 A2 | 11/2008 |

(Continued)

OTHER PUBLICATIONS

Peleg et al, Proc. Nat. Acad. Sci. USA, vol. 96, pp. 6700-6704 (Jun. 1999).*

(Continued)

*Primary Examiner* — Robert T Crow
(74) *Attorney, Agent, or Firm* — KPPB LLP

(57) ABSTRACT

Second harmonic nanoprobes for imaging biological samples and a method of using such probes to monitor the dynamics of biological process using a field resonance enhanced second harmonic (FRESH) technique are provided. The second harmonic generating (SHG) nanoprobes are comprised of various kinds of nanocrystals that do not possess an inversion symmetry and therefore are capable of generating second harmonic signals that can then be detected by conventional two-photon microscopy for in vivo imaging of biological processes and structures such as cell signaling, neuroimaging, protein conformation probing, DNA conformation probing, gene transcription, virus infection and replication in cells, protein dynamics, tumor imaging and cancer therapy evaluation and diagnosis as well as quantification in optical imaging.

14 Claims, 7 Drawing Sheets

(56) References Cited

U.S. PATENT DOCUMENTS

| | | | |
|---|---|---|---|
| 7,009,700 | B2 | 3/2006 | Dubois et al. |
| 7,679,079 | B1 | 3/2010 | Marks et al. |
| 7,813,016 | B2 | 10/2010 | Pu et al. |
| 7,993,891 | B2 | 8/2011 | Roitman et al. |
| 8,945,471 | B2 | 2/2015 | Pantazis et al. |
| 9,221,919 | B2 | 12/2015 | Pantazis et al. |
| 2003/0148391 | A1* | 8/2003 | Salafsky .............. 435/7.2 |
| 2004/0023415 | A1 | 2/2004 | Sokolov |
| 2004/0146460 | A1* | 7/2004 | Salafsky .............. 424/9.6 |
| 2005/0025422 | A1 | 2/2005 | Magnusson et al. |
| 2005/0186565 | A1 | 8/2005 | Malak |
| 2006/0056468 | A1* | 3/2006 | Dantus et al. .......... 372/28 |
| 2006/0228725 | A1 | 10/2006 | Salafsky |
| 2006/0289115 | A1 | 12/2006 | Zhao et al. |
| 2010/0233820 | A1 | 9/2010 | Pantazis |
| 2013/0129628 | A1 | 5/2013 | Pantazis |
| 2016/0051705 | A1 | 2/2016 | Pantazis et al. |

FOREIGN PATENT DOCUMENTS

| | | |
|---|---|---|
| WO | 2010090844 A2 | 8/2010 |
| WO | 2010090844 A3 | 11/2010 |
| WO | 2013078410 A1 | 5/2013 |

OTHER PUBLICATIONS

Loew, Pure and Appl. Chem., vol. 68, pp. 1405-1409 (1996).*

The definition of "centrosymmetric" provided by the online dictionary at AskDefine.com [retrieved on Jun. 25, 2012]. Retrieved from the Internet: <URL: http://centrosymmetric.askdefine.com/>.*

Corn et al, Chem. Rev., vol. 94, pp. 107-125 (1994).*

Averitt et al., "Linear optical properties of gold nanoshells", J. Opt. Soc. Am. B, Oct. 1999, vol. 16, No. 10, pp. 1824-1832.

Bastiaens et al., "Fluorescence lifetime imaging microscopy: spatial resolution of biochemical processes in the cell", trends in Cell Biology, Feb. 1999, vol. 9, pp. 48-52.

Greulich, "Fluorescence spectroscopy on single biomolecules", ChemPhysChem, 2005, vol. 6, pp. 2458-2471.

Lichtman et al., "Fluorescence microscopy", Nature Methods, Dec. 2005, vol. 2, No. 12, pp. 910-919.

Michalet et al., "The Power and Prospects of Fluorescence Microscopies and Spectroscopies", Annu. Rev. Biophys. Biomol. Struct., 2003, vol. 32, pp. 161-182.

Michalet et al., "Quantum Dots for Live Cells, in Vivo Imaging, and Diagnostics", www.sciencemag.org, Jan. 28, 2005, vol. 307, pp. 538-544.

Millar, "Fluorescence studies of DNA and RNA structure and dynamics", pp. 322-326.

Miyawaki, "Visualization of the Spatial and Temporal Dynamics of Intracellular Signaling", Developmental Cell, Mar. 2003, vol. 4, pp. 295-305.

Nie et al., "Probing Single Molecules and Single Nanoparticles by Surface-Enhanced Raman Scattering", Science, http://www.sciencemag.org, Feb. 21, 1997, vol. 275, pp. 1102-1106.

Peter et al., "Imaging molecular interactions by multiphoton FLIM", Biology of the Cell, 2004, vol. 96, pp. 231-236.

Piehler, "New methodologies for measuring protein interactions in vivo and in vitro", Current Opinion in Structural Biology, 2005, vol. 15, pp. 4-14.

Shaner et al., "A guide to choosing fluorescent proteins", Nature Methods, Dec. 2005, vol. 2, No. 12, pp. 905-909.

So et al., "Self-illuminating quantum dot conjugates for in vivo imaging", Nature Biotechnology, Mar. 2006, vol. 24, No. 3, pp. 339-343.

Suhling et al., "Time-resolved fluorescence microscopy", Photochem. Photobiol. Sci., 2005, vol. 4, pp. 13-22.

Sun, "Higher Harmonic Generation Microscopy", Adv Biochem Engin/Biotechnol, 2005, vol. 95, pp. 17-56.

Trifonov et al., "Ultrafast Energy Transfer and Structural Dynamics in DNA", J. Phys. Chem. B, 2005, vol. 109, pp. 19490-19495.

Truong et al., "The use of FRET imaging microscopy to detect protein-protein interactions and protein conformational changes in vivo", pp. 573-575.

Wallrabe et al., "Imaging protein molecules using FRET and FLIM microscopy", Current Opinion in Biotechnology, 2005, vol. 16, pp. 19-27,.

Whitesides, "The 'right' size in nanobiotechnology", Nature Biotechnology, Oct. 2003, vol. 21, No. 10, pp. 1161-1165.

Williams et al., "Fast Events in Protein Folding: Helix Melting and Formation in a Small Peptide", Biochemistry, 1996, vol. 35, pp. 691-697.

Zal et al., "Using live FRET imaging to reveal early protein-protein interactions during T cell activation", Current Opinion in Immunology, 2004, vol. 16, pp. 418-427.

Brauns et al., "Complex Local Dynamics in DNA on the Picosecond and Nanosecond Time Scales", Physical Review Letters, Apr. 15, 2002, vol. 88, No. 15, pp. 158101-1-158101-4.

Callender et al., "Fast Events in Protein Folding: The Time Evolution of Primary Processes", Annu. Rev. Phys. Chem., 1998, vol. 49, pp. 173-202.

Campagnola et al., "Second-harmonic imaging microscopy of living cells", Journal of Biomedical Optics, Jul. 2001, vol. 6, No. 3, pp. 277-286.

Cheatham, "Simulation and modeling of nucleic acid structure, dynamics and interactions", Current Opinion in Structural Biology, 2004, vol. 14, pp. 360-367.

Chen et al., "Protein localization in living cells and tissues using FRET and FLIM", International Society of Differentiation, 2003, vol. 71, pp. 528-541.

Day et al., "Imaging Molecular Interactions in Living Cells", Molecular Endocrinology, Jul. 2005, vol. 19, No. 7, pp. 1675-1686.

Denk et al., "Two-Photon Laser Scanning Fluorescence Microscopy", Science, New Series, Apr. 6, 1990, vol. 248, No. 4951, pp. 73-76.

Ding et al., "Direct Observation of Protein Folding, Aggregation, and a Prion-like Conformational Conversion", The Journal of Biological Chemistry, Dec. 2, 2005, vol. 280, No. 48, pp. 40235-40240.

Dobson, "The structural basis of protein folding and its links with human disease", Phil. Trans. R. Soc. Lond. B, 2001, vol. 356, pp. 133-145.

Dubertret et al., "In Vivo Imaging of Quantum Dots Encapsulated in Phospholipid Micelles", www.sciencemag.org, Science, Nov. 29, 2002, vol. 298, pp. 1759-1762.

Giepmans et al., "The Fluorescent Toolbox for Assessing Protein Location and Function", www.sciencemag.org, Science Apr. 14, 2006, vol. 312, pp. 217-224.

Gilmanshin et al., "Fast events in protein folding: Relaxation dynamics of secondary and tertiary structure in native apomyoglobin", Proc. Natl. Acad. Sci. USA, Apr. 1997, vol. 94, pp. 3709-3713.

Jares-Erijman et al., "FRET imaging", Nature Biotechnology, Nov. 2003, vol. 21, No. 11, pp. 1387-1395.

International Search Report for International Application No. PCT/US2007/085407 filed Nov. 21, 2007, Report completed Oct. 20, 2008, mailed Oct. 31, 2008, 2 pgs.

Written Opinion for International Application No. PCT/US2007/085407, filed Nov. 21, 2007, Opinion completed Oct. 20, 2008, mailed Oct. 31, 2007, 7 pgs.

Cohen, "Beyond fluorescence", Nature, Sep. 23, 2010, vol. 467, pp. 407-408.

Dombeck et al., "Optical Recording of Fast Neuronal Membrane Potential Transients in Acute Mammalian Brain Slices by Second-Harmonic Generation Microscopy", J. Neurophsiol. 2005, vol. 94, pp. 3628-3636.

Dworczak et al., "Electric field induced second harmonic generation (EFISH) experiments in the swivel cell: New aspects of an established method", Phys. Chem. Chem. Phys., 2000, vol. 2, pp. 5057-5064.

Franken et al., "Generation of Optical Harmonics", Physical Review Letters, Aug. 15, 1961, vol. 7, No. 4, pp. 118-120.

Girling et al., "Surface plasmon enhanced SHG from a hemicyanine monolayer", J. Phys. D: Appl. Phys., 1986, vol. 19, pp. 2065-2075.

(56) References Cited

OTHER PUBLICATIONS

Li et al., "Second harmonic generation in transparent KTiOPO$_4$/SiO$_2$ nanocomposite glasses prepared by the sol-gel method", Journal of Non-Crystalline Solids, 2000, vol. 261, pp. 273-276.
Maiman, "Stimulated Optical Radiation in Ruby", Nature, Aug. 6, 1960, vol. 187, pp. 493-494.
Vogt et al., "Optical Second Harmonic Generation in Sodium Nitrite", phys. stat. sol. (a), 1970, vol. 1, pp. 439-450.
International Search Report and Written Opinion for International Application No. PCT/US2012/066391, completed Feb. 23, 2013, 8 pgs.
Baker et al., "Imaging Brain Activity with Voltage-and Calcium-Sensitive Dyes", Cellular and Molecular Neurobiology, Apr. 2005, vol. 25, No. 2, pp. 245-282.
Bannai et al., "Imaging the lateral diffusion of membrane molecules with quantum dots", Nature Protocols, 2006, vol. 1, No. 6, pp. 2628-2634.
Billinton et al., "Seeing the Wood through the Trees: A Review of Techniques for Distinguishing Green Fluorescent Protein from Endogenous Autofluorescence", Analytical Biochemistry, 2001, vol. 291, pp. 175-197.
Blanchard et al., "Eliminating membrane depolarization caused by the Alzheimer peptide (A_(1-42, aggr.)", Biochemical and Biophysical Research Communications, 2002, vol. 293, pp. 1204-1208.
Bosnjak et al., "Towards preventive medicine", EMBO reports, 2008, vol. 9, No. 11, pp. 1056-1060.
Braslavsky et al., "Sequence information can be obtained from single DNA molecules", PNAS, Apr. 1, 2003, vol. 100, No. 7, pp. 3960-3964.
Bruchez, Jr. et al., "Semiconductor Nanocrystals as Fluorescent Biological Labels", Science, Sep. 25, 1998, vol. 281, pp. 2013-2016.
Campagnola et al., "Second-harmonic imaging microscopy for visualizing biomolecular arrays in cells, tissues and organisms", Nature Biotechnology, Nov. 2003, vol. 21, No. 11, pp. 1356-1360.
Chan et al., "Quantum Dot Bioconjugates for Ultrasensitive Nonisotopic Detection", Science, Sep. 25, 1998, vol. 281, pp. 2016-2018.
Dahan et al., "Diffusion Dynamics of Glycine Receptors Revealed by Single-Quantum Dot Tracking", Science, Oct. 17, 2003, vol. 302, pp. 442-445.
Dickson et al., "On/off blinking and switching behaviour of single molecules of green fluorescent protein", Nature, Jul. 24, 1997, vol. 388, pp. 355-358.
Empedocies et al., "Influence of Spectral Diffusions on the Line Shapes of Single CdSe Nanocrystallite Quantum Dots", J. Phys. Chem, 1999, vol. 103, pp. 1826-1830.
Hadjantonakis et al., "Technicolour Transgenics: Imaging Tools for Functional Genomics in the Mouse", Nature Reviews Genetics, Aug. 2003, vol. 4, pp. 613-627.
Hall, "Advanced sequencing technologies and their wider impact in microbiology", The Journal of Experimental Biology, 2007, vol. 209, pp. 1518-1525.
Harris et al., "Single-Molecule DNA Sequencing of a Viral Genome", Science, Apr. 4, 2008, vol. 320, pp. 106-109.
Hillier et al., "Whole-genome sequencing and variant discovery in c. elegans", Nature Methods, Feb. 2008, vol. 5, No. 2, pp. 183-188.
Kim et al., "Mitochondrial permeability transition: a common pathway to necrosis and apoptosis", Biochemical and Biophysical Research Communications, 2003, vol. 304, pp. 463-470.
Kirson et al., "Alternating electric fields arrest cell proliferation in animal tumor models and human brain tumors", PNAS, Jun. 12, 2007, vol. 104, No. 24, pp. 10152-10157.
Lander et al., "Initial sequencing and analysis of the human genome", Nature, Feb. 15, 2001, vol. 409, pp. 860-921.
Lippincott-Schwartz et al., "Studying Protein Dynamics in Living Cells", Nature, Jun. 2001, vol. 2, pp. 444-456.
Margulies et al., "Genome sequencing in microfabricated high-density picolitre reactors", Nature, Sep. 15, 2005, vol. 437, pp. 376-380.
McCaig et al., "Controlling Cell Behavior Electrically: Current Views and Future Potential", Physiol. Rev, 2005, vol. 85, pp. 943-978.
Michler et al., "Quantum correlation among photons from a single quantum dot at room temperature", Nature, Aug. 31, 2000, vol. 406, pp. 968-970.
Miyawaki, "Visualization of the Spatial and Temporal Dynamics of Intracelllular Signaling", Development Cell, Mar. 2003, vol. 4, pp. 295-305.
Nirmal et al., "Fluorescence intermittency in single cadmium selenide nanocrystals", Nature, Oct. 31, 1996, vol. 383, pp. 802-804.
Nuccitelli, "A Role for Endogenous Electric Fields in Wound Healing", Curr Top Dev Biol, 203, vol. 58, No. 1, pp. 1-24.
Pantazis, et al., "Second harmonic generating (SHG) nanoprobes for in vivo imaging", PNAS, Aug. 17, 2010, vol. 107, No. 33, pp. 14535-14540.
Pantazis et al., "Localized multiphoton photoactivation of paGFP in *Drosophila* wing imaginal discs", Journal of Biomedical Optics, Jul./Aug. 2007, vol. 12, No. 4, pp. 1-1-1-7.
Pelton et al., "Evidence for a diffusion-controlled mechanism for fluorescence blinking of colloidal quantum dots", PNAS, Sep. 4, 2007, vol. 104, No. 36, pp. 14249-14254.
Qiu et al., "Conducting Polyaniline Nanotubes by Template-Free Polymerization", Macromolecules, 2001, vol. 34, pp. 675-677.
Selvin, "The renaissance of fluorescence resonance energy transfer", Nature Structural Biology, Sep. 2000, vol. 7, No. 9, pp. 730-734.
Shendure et al., "Accurate Multiplex Polony Sequencing of an Evolved Bacterial Genome", Science, Sep. 9, 2005, vol. 309, pp. 1728-1732.
Shendure et al., "Advanced Sequencing Technologies: Methods and Goals", Nature Reviews Genetics, May 2004, vol. 5, pp. 335-344.
Shendure et al., "Overview of DNA Sequencing Strategies", Current Protocols in Molecular Biology, Jan. 2008, pp. 7.1.1-7.1.11.
Tsien, "Fluorescent Probes of Cell Signaling", Ann. Rev. Neurosci, 1989, vol. 2, pp. 227-253.
Venter et al., "The Sequence of the Human Genome", Science, Feb. 16, 2001, vol. 291, pp. 1304-1351.
Wang et al., "Non-blinking semiconductor nanocrystals", Nature, Jun. 4, 2009, vol. 459, pp. 686-689.
Zhao et al., "Electrical signals control wound healing through phosphatidylinositol-3-OH kinase-_and PTEN", Nature, Jul. 27, 2006, vol. 442, pp. 457-460.
International Search Report for International Application No. PCT/US2007/085409, filed Nov. 21, 2007, Report completed Oct. 7, 2008, mailed Oct. 10, 2008, 2 pgs.
Akerman et al., "Nanocrystal targeting in vivo", PNAS, Oct. 1, 2002, vol. 99, No. 20, pp. 12617-12621.
Alivisatos, "The use of nanocrystals in biological detection", Nature Biotechnology, Jan. 2004, vol. 22, No. 1, pp. 47-52.
Andreoni et al., "Holographic properties of the second-harmonic cross correlation of object and reference optical wave fields", J. Opt. Soc. Am., Jun. 2000, vol. 17, No. 6, pp. 966-972.
Chalfie et al., "Green Fluorescent Protein as a Marker for Gene Expression", Science, New Series, Feb. 11, 1994, vol. 263, No. 5148, pp. 802-805.
Chang et al., "An Efficient Approach to Derive Hydroxyl Groups on the Surface of Barium Titanate Nanoparticles to Improves tis Chemical Modification Ability", Journal of Colloid and Interface Science, 2009, 300-305.
Cuche et al., "Simultaneous amplitude-contrast and quantitative phase-contrast microscopy by numerical reconstruction of Fresnel off-axis holograms", Applied Optics, Dec. 1, 1999, vol. 38, No. 34, pp. 6994-7001.
Dobson, "Protein folding and misfolding", Nature, Dec. 18-25, 2003, vol. 426, pp. 884-890.
Dubois et al., "Improved three-dimensional imaging with a digital holography mircoscope with a source of partial spatial coherence", Applied Optics, Dec. 1, 1999, vol. 38, No. 34, pp. 7085-7094.
Gabor, "A New Microscopic Principle", Nature, May 15, 1948, No. 4098, pp. 777-778.

(56) References Cited

OTHER PUBLICATIONS

Gerlich et al., "4D imaging to assay complex dynamics in live specimens", Reviews, Sep. 2003, pp. S14-S19.

Jaiswal et al., "Use of quantum dots for live cell imaging", Nature Methods, Oct. 2004, vol. 1, No. 1, pp. 73-78.

Krenn et al., "Squeezing the Optical near-Field Zone by Plasmon Coupling of Metallic Nanoparticles", Physical Review Letters, Mar. 22, 1999, vol. 82, No. 12, pp. 2590-2593.

Kubelka et al., "The protein folding 'speed limit'", Current Opinion in Structural Biology, 2004, vol. 14, pp. 76-88.

Leith et al., "Microscopy of Wavefront Reconstruction", Journal of the Optical Society of America, Aug. 1965, vol. 55, No. 8, pp. 981-986.

Leith et al., "Wavefront Reconstruction with Diffused Illumination and Three-Dimensional Objects", Journal of the Optical Society of America, Nov. 1964, vol. 54, No. 11, pp. 1295-1301.

Loew, "Potentiometric dyes: Imaging electrical activity of cell membranes", Pure & Appl. Chem, 1996, vol. 88, No. 7. pp. 1405-1409.

Maier et al., "Optical pulse propagation in metal nanoparticle chain waveguides", Physical Review, 2003, vol. B67, pp. 205402-1 thru 205402-5.

Maletic-Savatic et al., "Rapid Dendritic Morphogenesis in CA1 Hippocampal Dendrites Induced by Synaptic Activity", Science, Mar. 19, 1999, vol. 283, pp. 1923-1927.

Marquet et al., "Digital holographic microscopy: a noninvasive contrast imaging technique allowing quantitative visualization of living cells with subwavelength axial accuracy", Optics Letters, Mar. 1, 2005, vol. 30, No. 5, pp. 468-470.

Miccio et al, "Direct full compensation of the aberrations in quantitative phase microscopy of thin objects by a single digital hologram", Applied Physics Letters, 2007, vol. 90, pp. 041104-1 thru 041104-3.

Miyawaki et al., "Dynamic and quantitative Ca2+ measurements using improved cameleons", Proc. Natl. Acad. Sci. USA, Mar. 1999, vol. 96, pp. 2135-2140.

Pedrini et al., "Aberration compensation in digital holographic reconstruction of microscopic objects", Journal of Modern Optics, 2001, vol. 48, No. 6, pp. 1035-1041.

Pollok et al., "Using GFP in FRET-based applications", Trends in Cell Biology, Feb. 1999, vol. 9, pp. 57-60.

Pu et al., "Four-dimensional dynamic flow measurement by holographic particle image velocimetry", Applied Optics, Dec. 20, 2005, vol. 44, No. 36, 7697-7708.

Pu et al., "Intrinsic aberrations due to Mie scattering in particle holography", J. Opt. Soc. Am, Oct. 2003, vol. 20, No. 10, pp. 1920-1932.

Sandrock et al., "Synthesis and Second-Harmonic Generation Studies of Noncentrosymmetric Gold Nanostructures", J. Phys. Chem. B, 1999, vol. 103, pp. 2668-2673.

Schnars et al., "Direct recording of holograms by a CCD target and numerical reconstruction", Applied Optics, Jan. 19, 1994, vol. 33, No. 2, pp. 179-181.

Shalaev, "Electromagnetic Properties of Small-Particle Composites", Physics Reports, 1996, 272, pp. 61-137.

Shi et al., "Rapid Spine Delivery and Redistribution of AMPA Receptors After Synaptic NMDA Receptor Activation", Science, Jun. 11, 1999, vol. 284, pp. 1811-1816.

Toth et al., "Reconstruction of a Three-Dimensional Microscopic Sample Using Holographic Techniques", Applied Physics Letters, Jul. 1, 1968, vol. 13 No. 1, p. 7-9.

Xu et al., "Tracking particles in four dimensions with in-line holographic microscopy", Optics Letters, Feb. 1, 2003, vol. 28, No. 3, pp. 164-166.

Yamaguchi et al., "Phase-shifting digital holography", Optics Letters, Aug. 15, 1997, vol. 22, No. 16, pp. 1268-1270.

Zayats et al., "Second-harmonic generation from individual surface defects under local excitation", Physical Review B, Feb. 15, 2000, vol. 61, No. 7, pp. 4545-4548.

Zhang et al., "Three-dimensional microscopy with phase-shifting digital holography", Optics Letters, Aug. 1, 1998, vol. 23, No. 15, pp. 1221-1223.

Zipfel et al., "Nonlinear magic: multiphoton microscopy in the biosciences", Nature Biotechnology, Nov. 2003, vol. 21, No. 11, pp. 1369-1377.

Ledoux et al., "Linear and nonlinear optical properties of n-4-nitrophenyl L-prolinol single crystals", Optics Communications, Dec. 15, 1990, vol. 80, No. 2, pp. 149-154.

Luo et al., "Mechanism of Linear and Nonlinear Optical Properties of the Urea Crystal Family", The Journal of Physical Chemistry, 2011, vol. 115, pp. 5192-5200.

Nikogosyan, "Nonlinear Optical Crystals: A Complete Survey", Springer Science+Business Media, Inc., 2005, ISBN 0-387-22022-4, 429 pgs.

* cited by examiner

FIG. 2

Two-Photon excited fluorescence vs Second Harmonic Generation

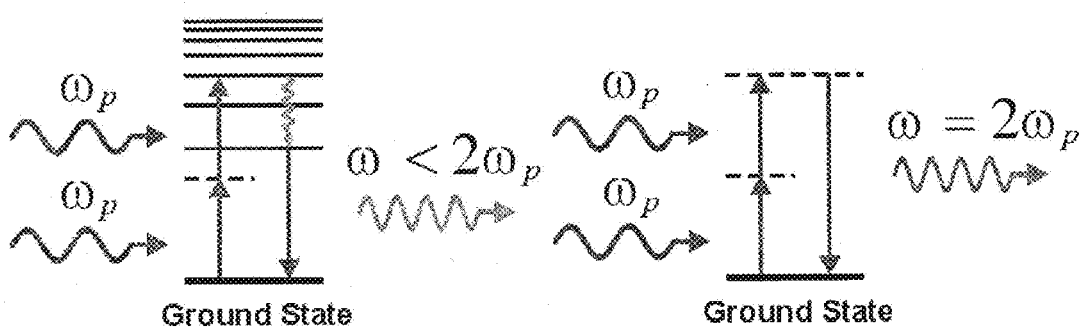

2-photon excited Fluorescence

- Involves real transition
- Energy is partially lost
- Nanosecond response time
- Frequency lower than second harmonic generation

Second Harmonic Generation

- Involves virtual transition
- Energy is conversed
- Femtosecond response time
- Frequency exactly doubled
- Requires ordered, noncentrosymmetric materials

SECOND HARMONIC IMAGING NANOPROBES AND TECHNIQUES FOR USE THEREOF

CROSS-REFERENCE TO RELATED APPLICATIONS

The current application claims priority to U.S. Provisional Application No. 60/860,439, filed Nov. 21, 2006, and U.S. Provisional Application No. 60/936,043, filed Jun. 18, 2007, the disclosures of which are incorporated herein by reference.

STATEMENT OF FEDERAL RIGHTS

The U.S. Government has certain rights in this invention pursuant to Grant No. HR0011-04-1-0032 awarded by DARPA and Grant Nos. HD043897 and HG004071 awarded by the National Institutes of Health.

FIELD OF THE INVENTION

The current invention is directed to a methodology for imaging biological samples using second harmonic generating nanoprobes.

BACKGROUND OF THE INVENTION

One of the grand open challenges in modern science is to identify cells or probe molecules and understand the mechanism and dynamics of biological processes at the molecular level with high sensitivity and spatiotemporal resolution, and particularly inside living cells and tissue or liquid. As a result of the wealth of information potentially accessible from such biological targets, there has been a growing demand for imaging tools for biomedical research and medicine. This research has led to the development of new techniques like magnetic resonance imaging (MRI), ultrasound, positron emission tomography (PET), and optical coherence tomography (OCT). However, these techniques require high costs and some fundamental technological barriers hinder their widespread use.

Optical imaging is a recent technique that utilizes photons as an information source with applications in a wide range of basic science and clinical studies like pharmacology, cellular biology, and diagnostics. For example, semiconductor nanocrystals, small organic dyes or fluorescent proteins are commonly used as optical labels in in vivo optical imaging. (See, e.g., X. Michalet et al., Science 307, 538 (Jan. 28, 2005); B. Dubertret et al., Science 298, 1759 (Nov. 29, 2002); M. K. So, C. Xu, A. M. Loening, S. S. Gambhir, J. Rao, Nat Biotechnol 24, 339 (March, 2006); N. C. Shaner, P. A. Steinbach, R. Y. Tsien, Nat Methods 2, 905 (December, 2005); and B. N. Giepmans, S. R. Adams, M. H. Ellisman, R. Y. Tsien, Science 312, 217 (Apr. 14, 2006), the disclosures of which are incorporated herein by reference.) Indeed, recent advances in fluorescence microscopy alone have profoundly changed how cell and molecular biology is studied in almost every aspect. (For example, see, Lichtman, J. W. & Conchello, J. A. Nat. Methods 2, 910-919 (2005); Michalet, X. et al. Annu. Rev. Biophys. Biomolec. Struct. 32, 161-182 (2003); Jares-Erijman, E. A. & Jovin, T. M. Nat. Biotechnol. 21, 1387-1395 (2003); Bastiaens, P. I. H. & Squire, A., Trends Cell Biol. 9, 48-52 (1999); and Suhling, K., et al, Photochem. Photobiol. Sci. 4, 13-22 (2005), the disclosures of which are incorporated herein by reference.)

However, the ultimate need of characterizing biological targets is largely unmet due to fundamental deficiencies associated with the use of fluorescent agents. For example, fluorescent probes face two major limitations that have a significant impact on the signal strength: 1) dye saturation, because the number of photons emitted by the fluorophore in a given time is restricted by the excited state lifetime, and 2) dye bleaching, which limits the total number of photons per dye. In addition, autofluorescence from tissue organic components due to illumination absorption can severely limit the signal-to-noise ratio. Finally, fluorescence is fundamentally an optically incoherent process, and as a result extracting 3D information from the source is inherently difficult.

Accordingly, a need exists for a new probe for imaging/detecting biological structures and processes that avoids the inherent technological limitations found in the fluorescent imaging techniques of the prior art.

SUMMARY OF THE INVENTION

The current invention is directed to nanoprobes for imaging/detecting structures and biological processes based on a novel second harmonic (SH) technique.

In one embodiment, the probe nanostructures that generate second harmonic signals emit coherent waves for imaging biological structures without bleaching, blinking or saturation.

In another embodiment, the probe nanostructures are attached to molecules of interest or delivered to cells of interest.

In another embodiment, the probes of the current invention are formed of two dissimilar types of nanostructures: a first exciter nanostructure that resonates at the frequency of the pump, and a second probe nanostructure that generates second harmonic signals.

In still another embodiment the first exciter nanostructure is a metal nanostructure and the second probe nanostructure is a nanocrystal.

In yet another embodiment, the exciter nanostructure is chosen such that when pumped via a continuous wave, modulated or pump source it enhances the electric field within a few nanometers of its vicinity. In such an embodiment, the enhanced local field can couple with neighboring probes, and the short-range interactions can then be used as a nanometer sensitive distance gauge.

In still yet another embodiment, the current invention is directed to a method of imaging/detecting with superb sensitivity and spatiotemporal resolution biological process and structures using a field resonance enhanced second harmonic (FRESH) technique.

In still yet another embodiment, the current invention is directed to a method of using the SH nanoprobes in a detection scheme, such as, the rapid detection of a specific target, the imaging/detection of medical conditions or neoplasm, and the detection or tracking of a therapeutic agent.

BRIEF DESCRIPTION OF THE DRAWINGS

The description and claims of the current invention will be more fully understood with reference to the following figures and data graphs, which are presented as exemplary embodiments of the invention and should not be construed as a complete recitation of the scope of the invention, wherein:

FIG. 2 provides a schematic diagram comparing the properties of the second harmonic technique of the current invention with the fluorescence used in conventional optical systems;

DETAILED DESCRIPTION OF THE INVENTION

Figure 1A:
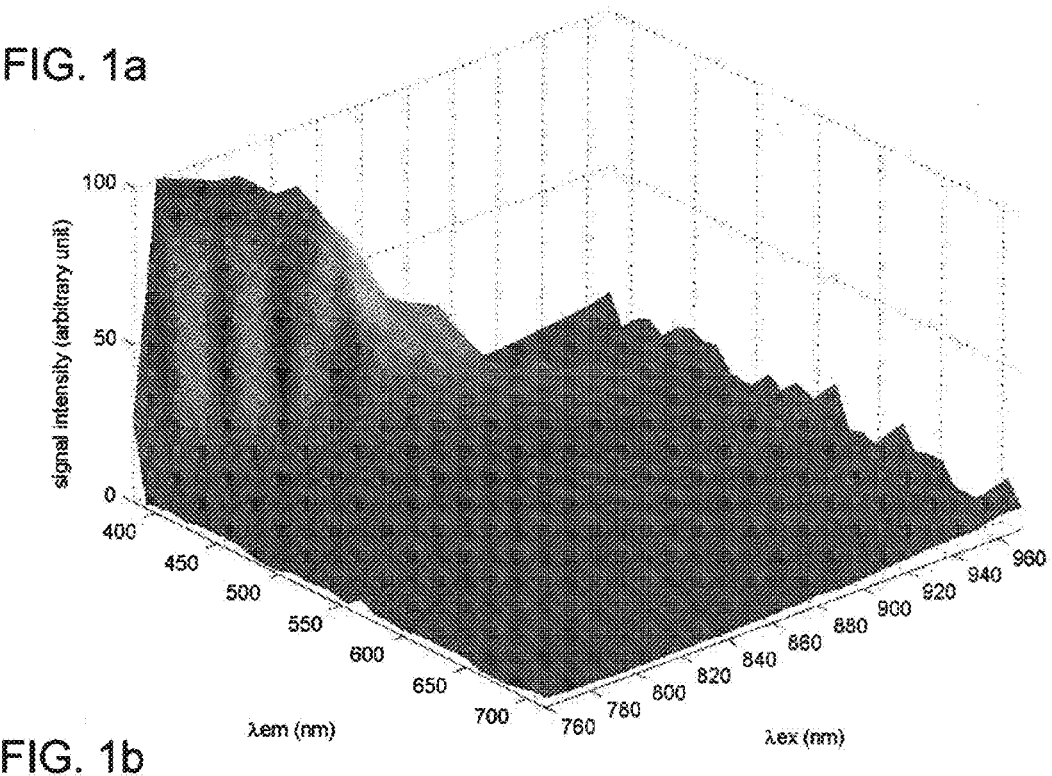
FIGS. 1a & 1b provide emission profiles of an exemplary second harmonic generation nanocrystal probe in accordance with the current invention.

The current invention is generally directed to a methodology for imaging/detecting biological samples using nanoprobes capable of producing a second harmonic generation response. In addition, the application is directed to a technique for dynamic imaging/detecting dynamic processes like molecule conformation changes or molecule-molecule interactions using a field resonance enhanced second harmonic technique; referred to from hereinafter as FRESH. Both the SHG nanoprobes and the FRESH imaging technique is designed to overcome the shortcomings of conventional fluorescence-based techniques.

Specifically, to overcome the limitations inherent in conventional imaging techniques, the current invention is drawn to an imaging methodology that uses second harmonic generating (SHG) nanoprobes that are suitable for (in vivo/in vitro) imaging/detecting and can avoid most of the inherent drawbacks encountered in classical optical systems. The key element of this invention is based on labeling molecules or identifying cells of interest with nonlinear materials, e.g., various kinds of inorganic and/or organic nanocrystals that do not possess an inversion symmetry and therefore are capable of generating second harmonic signals.

For typical tissue such emissions might range, for example, from 350 to 700 nm, although other wavelengths might be used dependent on the material to be imaged. These emissions can then be detected by any optical based technique, such as, for example, conventional two-photon microscopy (for example, for wavelengths in the range of 350 to 700 nm by tuning the wavelength from 700 to 1400 nm), or continuous wave, modulated, or other pulsed lasers having for example nano, pico, femto, or attosecond timeframes.

As discussed above, the basic principle behind the SH nanoprobes of the current invention is to attach to a molecule of interest a probe nanostructure that generates a second harmonic signal or to identify cells or tissue of a living subject (in vivo/in vitro) using such probe nanostructures. Such a structure may be any organic, inorganic or combination of organic and inorganic nanocrystal, such as, for example $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, $Fe(IO_3)_3$, N-(4 nitrophenyl)-(L)-prolinol (NPP), urea, 4-Nitroaniline, 2-Methyl-4-nitroaniline (MA), 3-Methyl-4-methoxy-4'-nitrostilbene), β-BaB2O4 (Beta-Barium Borate/BBO), LiB3O5 (Lithium Triborate/LBO), LiNbO3 (Lithium Niobate/LN), KTiOPO4 (Potassium Titanyl Phosphate/KTP), AgGaS2 (Silver Thiogallate/AGS), AgGaSe2 (Silver Gallium Selenide/AGSe), ZnGeP2 (Zinc Germanium Phosphide/ZGP), GaSe (Gallium Selenide), KH2PO4 (Potassium Dihydrogen Phosphate/KDP), NH4H2PO4 (Ammonium Dihydrogen Phosphate (ADP), KD2PO4 (Deuterated Potassium Dihydrogen Phosphate/DKDP), CsLiB6O10 (Cesium Lithium Borate/CLBO), KTiOAsO4 (Potassium Titanyl Arsenate/KTA), KNbO3 (Potassium Niobate/KN), LiTaO3 (Lithium Tantalate/LT), RbTiOAsO4 (Rubidium Titanyl Arsenate/RTA), BaTiO3 (Barium Titanate), MgBaF4 (Magnesium Barium Fluoride), GaAs (Gallium Arsenide), BiB3O6 (Bismuth Triborate/BIBO), K2Al2B2O7 (Potassium Aluminum Borate/KABO), KBe2BO3F2 (Potassium Fluoroboratoberyllate/KBBF), BaAlBO3F2 (Barium Aluminum Fluoroborate/BABF), La2CaB10O19 (Lanthanum Calcium Borate/LCB), GdCa4O(BO3)3 (Gadolinium Calcium Oxyborate/GdCOB), YCa4O(BO3)3 (Yttrium Calcium Oxyborate/YCOB), Li2B4O7 (Lithium Tetraborate/LB4), LiRbB4O7 (Lithium Rubidium Tetraborate/LRB4), CdHg(SCN)4 (Cadmium Mercury Thiocyanate/CMTC), RbTiOPO4 (Rubidium Titanyl Phosphate/RTP), LiInS2 (Lithium Thioindate/LIS), LiInSe2 (Lithium Indium Selenide/LISe), KB5O8 4H2O (Potassium Pentaborate Tetrahydrate/KB5), CsB3O5 (Cesium Triborate/CBO), C4H7D12N4PO7 (Deuterated L-Arginine Phosphate Monohydrate/DLAP), a-HIO3 (a-Iodic Acid), LiCOOH H2O (Lithium Formate Monohydrate/LFM), CsH2AsO4 (Cesium Dihydrogen Arsenate/CDA), CsD2AsO4 (Deuterated Cesium Dihydrogen Arsenate/DCDA), RbH2PO4 (Rubidium Dihydrogen Phosphate/RDP), CsTiOAsO4 (Cesium Titanyl Arsenate/CTA), Ba2NaNb5O15 (Barium Sodium Niobate/BNN), K3Li2Nb5O15 (Potassium Lithium Niobate/KLN), CO(NH2)2 (Urea), LiIO3 (Lithium Iodate), Ag3AsS3 (Proustite), HgGa2S4 (Mercury Thiogallate), CdGeAs2 (Cadmium Germanium Arsenide/CGA), Ti3AsSe3 (Thallium Arsenic Selenide/TAS), CdSe (Cadmium Selenide), ZnO (Zinc Oxide), ZnS (Zinc Sulfide), ZnSe (Zinc Selenide), ZnTe (Zinc Telluride), CdS (Cadmium Sulfide), SiC (Silicon Carbide), GaN (Gallium Nitride), and GaSb (Gallium Antimonide), among others.

In turn, the molecule of interest may be, for example, a protein, DNA, RNA, a cell or tissue. If the molecule of interest is a cell, such a cell may be, for example, a cancer cell, stem cell, or tumor.

Although a few specific examples of possible probe nanostructure nanocrystals are described above, it should be understood that any nanostructure, defined hereinafter as a structure of ≤10 μm, capable of second harmonic generation may be used in the current invention. The requirement of the materials, as discussed above, being that the nanostructure not possess an inversion symmetry center.

Figure 1B:
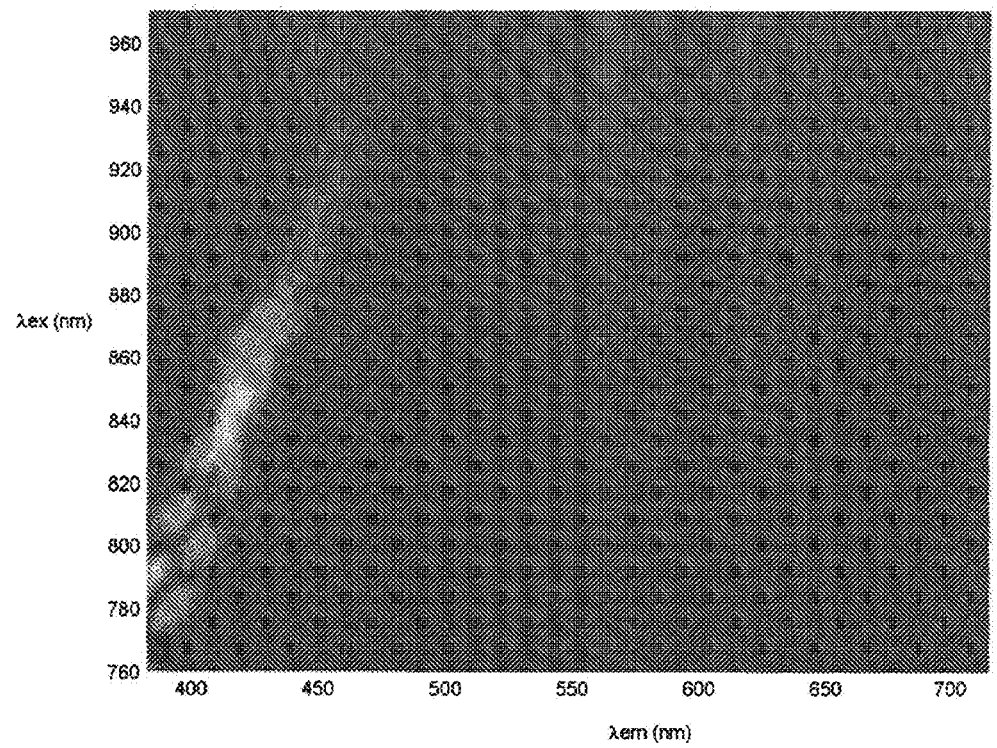

FIG. 1 provides an exemplary data graph for a second harmonic emission profile generated from BaTiO$_3$-nanocrystals in accordance with the current invention. As shown, the second harmonic emission ranges from 380 to 485 nm displaying, unlike many other optical probes, discrete emission peaks of around 10 nm, and was generated by conventional two-photon excitation, where the excitation energy ranges from 760 to 970 nm.

Although only single types of SH nanoprobes are discussed above, it should be understood that a plurality of SH nanoparticles displaying distinct emission profiles can be used to identify various labeled molecules or cells of interest in parallel. Although one exemplary excitation profile generated through standard two-photon excitation is provided in FIG. 1, it should be understood that any conventional excitation source may be used that is compatible with second harmonic generation.

Second harmonic generation has many inherent advantages over fluorescence that open the possibility of a wide variety of applications. These advantages are discussed with reference to the schematic diagram provided in FIG. 2.

First, as a parametric nonlinear optical process, second harmonic generation does not involve real electron energy transition but only virtual transitions. Fluorescence, on the other hand, involves actual energy transition of electrons. As a result, the response time of second harmonic generation is at the femtosecond level, about four to five orders of magnitude faster than the nanosecond response time of fluorescence, allowing very fast and sensitive detection of molecules with appropriate detection systems. (See, e.g., R. W. Boyd, *Nonlinear optics* (Academic Press, San Diego, Calif., ed. 2nd, 2003), pp. xvii, 578 p, the disclosure of which is incorporated herein by reference.)

Second, biological tissue does not often assemble into large, ordered noncentrosymmetric structures. As a result, biological tissue does not generate a strong SH signal, therefore, the second harmonic generating crystals can be imaged with sharp contrast (high signal-to-noise ratio) when presenting in vivo, allowing detection of single nanocrystals attached to molecules of interest or identification of cells of interest harboring a nanocrystal in tissue.

Figure 3:
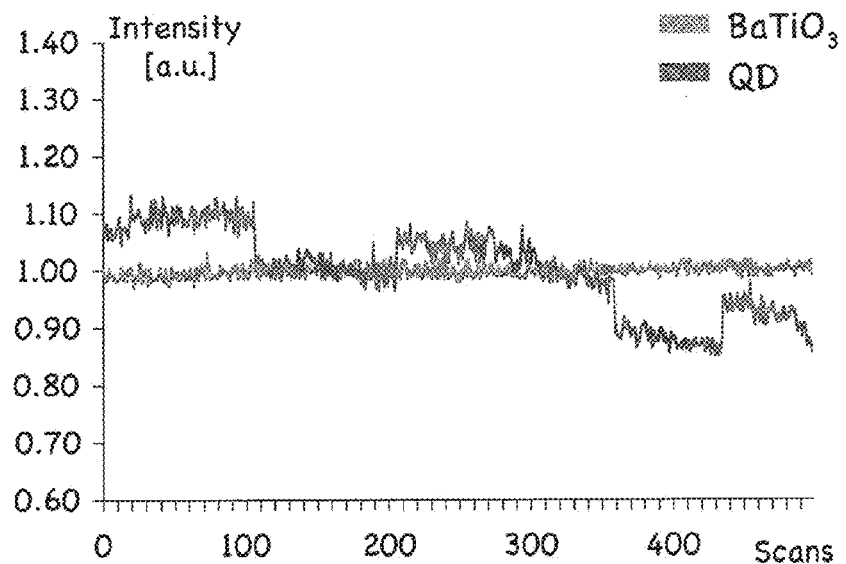
FIG. 3 provides a set of data graphs showing the comparative bleaching and blinking properties for an exemplary second harmonic generation nanocrystal probe in accordance with the current invention and a conventional quantum dot.

Third, unlike fluorescent dyes, second harmonic generating nanocrystals do not undergo photo-bleaching or blinking, as shown in FIG. 3. In this set of data graphs, SHG single BaTiO$_3$ nanocrystals and CdSe/ZnS quantum dots (QD) were immobilized in 20% polyacrylamide and illuminated 500 times within 25 s with 820 nm light. As shown, whereas the QD signal fluctuates displaying blinking and photobleaching, the second harmonic signal intensity of BaTiO$_3$ is constant, making it a superior single molecule detection probe. (See, e.g., W. Denk, J. H. Strickler, W. W. Webb, *Science* 248, 73 (Apr. 6, 1990), the disclosure of which is incorporated herein by reference.)

Figure 4:
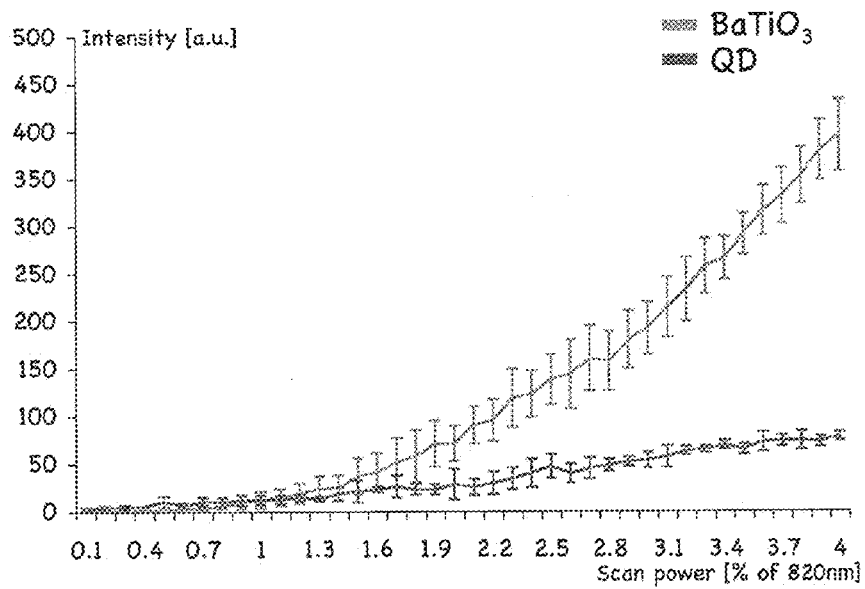
FIG. 4 provides a set of data graphs showing the saturation properties for an exemplary second harmonic generation nanocrystal probe in accordance with the current invention and a conventional quantum dot.

Fourth, again unlike fluorescent dyes, SHG nanocrystals do not undergo photo-saturation with increasing illumination intensity, as shown in FIG. 4. In this set of data graphs, BaTiO$_3$ nanocrystals and CdSe/ZnS quantum dots (QD) were immobilized in 20% polyacrylamide and illuminated with increasing 820 nm light intensity. As shown, signal saturation of QD occurs already at very low power levels, whereas the second harmonic signal of BaTiO$_3$ nanocrystals increases quadratically, allowing very efficient visualization or detection of, for example, a single molecule attached to such as a nanoprobe crystal, for example, in tissue or sample solution by simply increasing the illumination power. (See, e.g., C. K. Sun, *Adv Biochem Eng Biotechnol* 95, 17 (2005), the disclosure of which is incorporated herein by reference.)

Finally, the SHG nanocrystal probes of the current invention show a high pH stability allowing targeting a wider range of molecules of interest, such as, for example, acidic organelles without signal loss.

The biocompatibility of the technique was also studied, and it has been shown that injected embryos developed indistinguishably from uninjected counterparts.

Although only specific embodiments of the invention are discussed above and in the examples below, it should be understood that the unique combination of properties possessed by the second harmonic nanoprobes of the current invention allows for a number of applications including, for example; protein, DNA, RNA and tumor imaging and cancer or stem cell therapy evaluation and diagnosis as well as quantification in optical imaging, (in vivo/in vitro) imaging of biological processes such as cell signaling, neuroimaging, protein conformation probing, DNA conformation probing, gene transcription, and virus infection and replication in cells. In addition the SHG nanoprobes of the current invention may be used to for a number of (in vivo/in vitro) imaging applications.

Example 1

SH Nanoprobe Imaging

Figure 5:
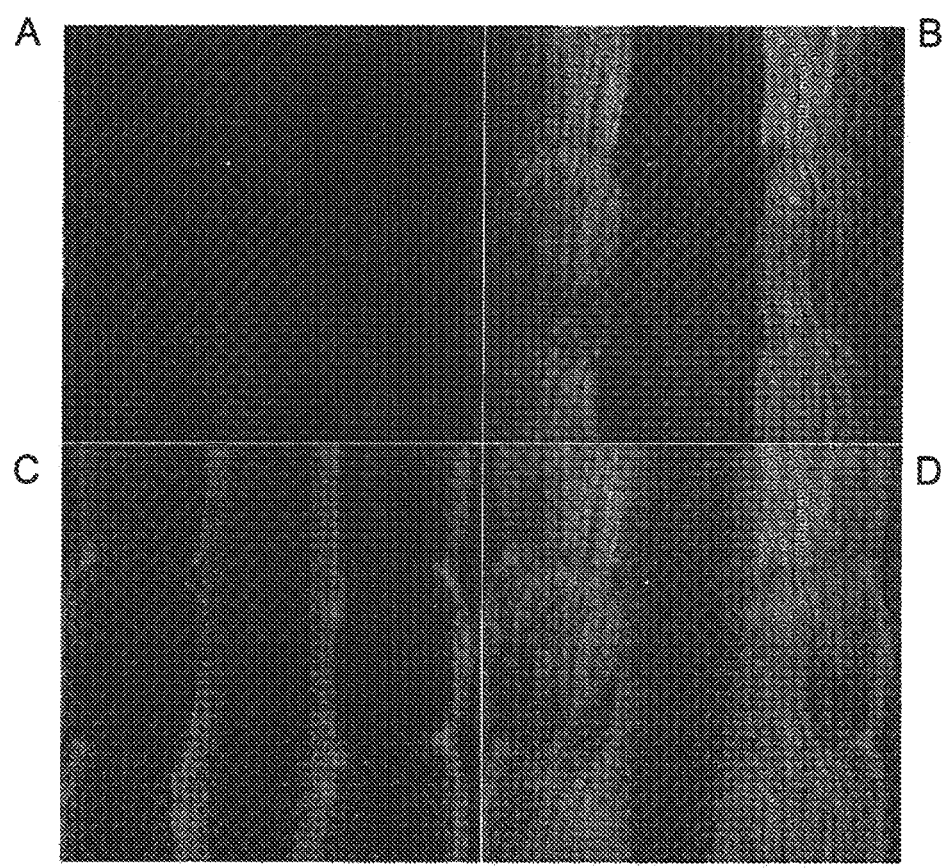
FIGS. 5a to 5d provide photographs exhibiting the in vivo imaging properties of an exemplary second harmonic generation nanocrystal probe in accordance with the current invention.

To demonstrate the superior imaging properties of the SHG nanocrystal probes of the current invention, BaTiO3 nanocrystals were injected into zebrafish embryos. Two days after cytoplasmic injection the nanocrystals were excited with femtosecond pulsed 820 nm light. As shown in the photographic plates provided in FIGS. 5A to 5D, the low energy excitation of the probe nanocrystals results in a strong second harmonic signal (the bright point of light in the center of the image in FIG. 5A). This signal is detectable in epi-mode (FIG. 5A) as well as in trans-mode (FIG. 5B) throughout the whole zebrafish body (nanocrystal indicated at arrowhead in figures), proving the coherence of the technique. In contrast, the endogenous second harmonic signal from the tail-muscles can only be detected with relatively high energy excitation in the trans-mode (FIG. 5B). (For discussion, see, e.g., P. J. Campagnola, L. M. Loew, *Nat Biotechnol* 21, 1356 (November, 2003); and P. J. Campagnola, et al., *J Biomed Opt* 6, 277 (July, 2001)., the disclosures of which are incorporated herein by reference.) FIG. 5C provides an image developed from injecting a conventional Bodipy TR methyl ester dye to label the extracellular matrix and cell membranes. FIG. 5D provides a merged picture showing the signal from the inventive probe combined with the images of the tissue developed from other techniques.

This exemplary image shows that the SHG nanocrystal probes of the current invention provide superb signal-to-noise ratio after in vivo injections allowing detection in rather deep organs, as well as the potential for real-time biodistribution monitoring. In addition, unlike endogenous second harmonic generation from ordered, noncentrosymmetric structures like collagen or myosin, which can only be detected in trans-mode, SHG nanocrystals can be detected both in trans-mode as well as in epi-mode allowing for the ability to isolate the probe signal from the background signal generated by the surrounding biological structures.

Example 2

Field Resonance Enhanced Second Harmonic Technique

In addition to simple second harmonic imaging using the second harmonic generating nanoprobes of the current invention, the nanoprobes may also be used in a field resonance enhanced mode to allow access to a number of biological processes that can occur below the nanosecond time frame. Using this field resonance enhanced second harmonic (FRESH) technique in accordance with the current invention it is possible to examine the dynamics of biological processes with high sensitivity and spatiotemporal resolution.

To understand the potential importance of the FRESH technique it is necessary to examine the inner workings of most biological processes. Besides having highly complex three-dimensional (3D) structures spanning a large range of length scales, living organisms by their nature are very dynamic: molecular processes such as protein, DNA, and RNA conformations—that take place in a timescale ranging from 100 fs to 100 s while the organisms move and metabolize—as well as molecule-molecule interactions such as, but not limited to, protein-protein, protein-DNA, and protein-RNA interactions. (See, e.g., Whitesides, G. M., Nat. Biotechnol. 21, 1161-1165 (2003); Williams, S. et al., Biochemistry 35, 691-697 (1996); Gilmanshin, R., et al., Proc. Natl. Acad. Sci. U.S.A. 94, 3709-3713 (1997); Callender, R. H., et al., Annual Review of Physical Chemistry 49, 173-202 (1998); Trifonov, A. et al., Journal of Physical Chemistry B 109, 19490-19495 (2005); Cheatham, T. E., Curr. Opin. Struct. Biol. 14, 360-367 (2004); Millar, D. P., Curr. Opin. Struct. Biol. 6, 322-326 (1996); and Brauns, E. B., et al., Physical Review Letters 88 (2002), the disclosures of which are incorporated herein by reference.) The understanding of these processes not only has fundamental biological significance, but could also enable the treatment of a host of human diseases. For example, it has been shown that a variety of serious diseases can be directly linked to protein misfolding. (See, e.g., Ding, F., et al., J. Biol. Chem. 280, 40235-40240 (2005); and Dobson, C. M., Philos. Trans. R. Soc. Lond. B 356, 133-145 (2001), the disclosures of which are incorporated herein by reference.)

Fluorescence resonance energy transfer (FRET) and its associated techniques have achieved great success in probing molecular activities. (See, e.g., Selvin, P. R. Nat. Struct. Biol. 7, 730-734 (2000); Greulich, K. O., ChemPhysChem 6, 2458-2471 (2005); Peter, M. & Ameer-Beg, S. M. FLIM. Biol. Cell 96, 231-236 (2004); Day, R. N. & Schaufele, F., Mol. Endocrinol. 19, 1675-1686 (2005); Wallrabe, H. & Periasamy, A., Curr. Opin. Biotechnol. 16, 19-27 (2005); Piehler, J., Curr. Opin. Struct. Biol. 15, 4-14 (2005); Chen, Y., et al., Differentiation 71, 528-541 (2003); Truong, K. & Ikura, M. Curr. Opin. Struct. Biol. 11, 573-578 (2001); Zal, T. & Gascoigne, N. R., Curr. Opin. Immunol. 16, 418-427 (2004); and Miyawaki, A., Dev. Cell 4, 295-305 (2003), the disclosures of which are incorporated herein by reference.) However, these techniques still have the same basic limitations of fluorescence discussed above, including blinking, bleaching, and saturation, which restricts the sensitivity, signal-to-noise ratio, and spatiotemporal resolution. The integration of the nanoprobes of the current invention with a field resonance enhancement technique in the FRESH protocol set forth herein allows for greatly improved capabilities for the spatiotemporal visualization/detection of (single) molecule conformation changes or molecule-molecule interactions.

Figure 6:
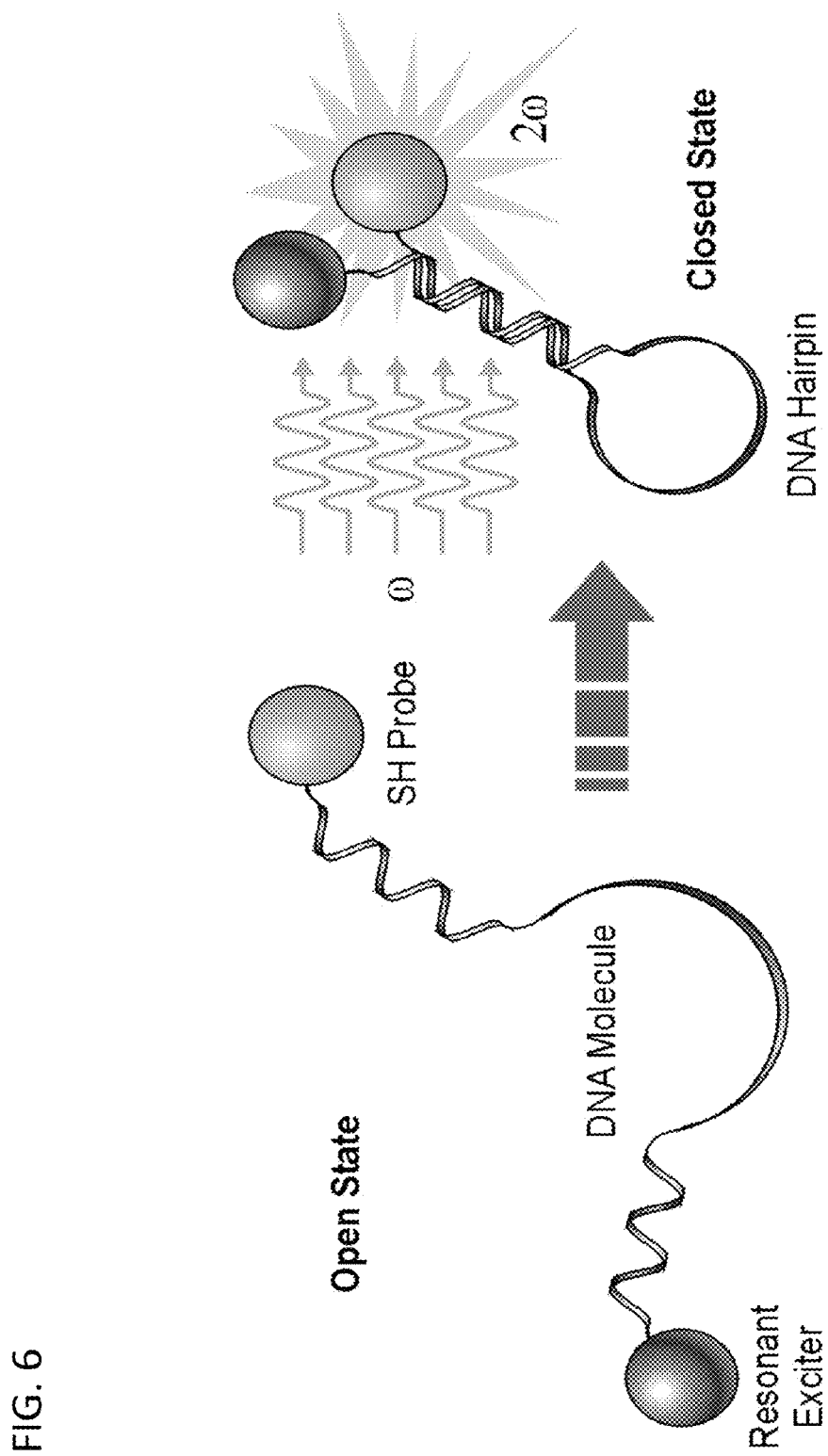
FIG. 6 provides a schematic diagram of the principles of operation of an exemplary embodiment of the second harmonic generation nanocrystal probe imaging technique in accordance with the current invention.

The basic principle of the FRESH technique is illustrated in FIG. 6, where a simple DNA hairpin molecule is used as an example. In the FRESH methodology, two dissimilar types of nanostructures are used to label molecules of interest. First, an exciter nanostructure that resonates at the frequency of the pump is attached to the molecule. Such a structure may be a metal nanostructure, such as, for example, Au-nanorods, Au-nanospheres or Au-nanoshells, and other materials as well. Second, a probe nanostructure that generates a second harmonic signal in accordance with the current invention is attached to the molecule. As before such a probe nanostructure can be any construct organic, inorganic or a combination thereof that does not possess an inversion symmetry.

Figure 7:
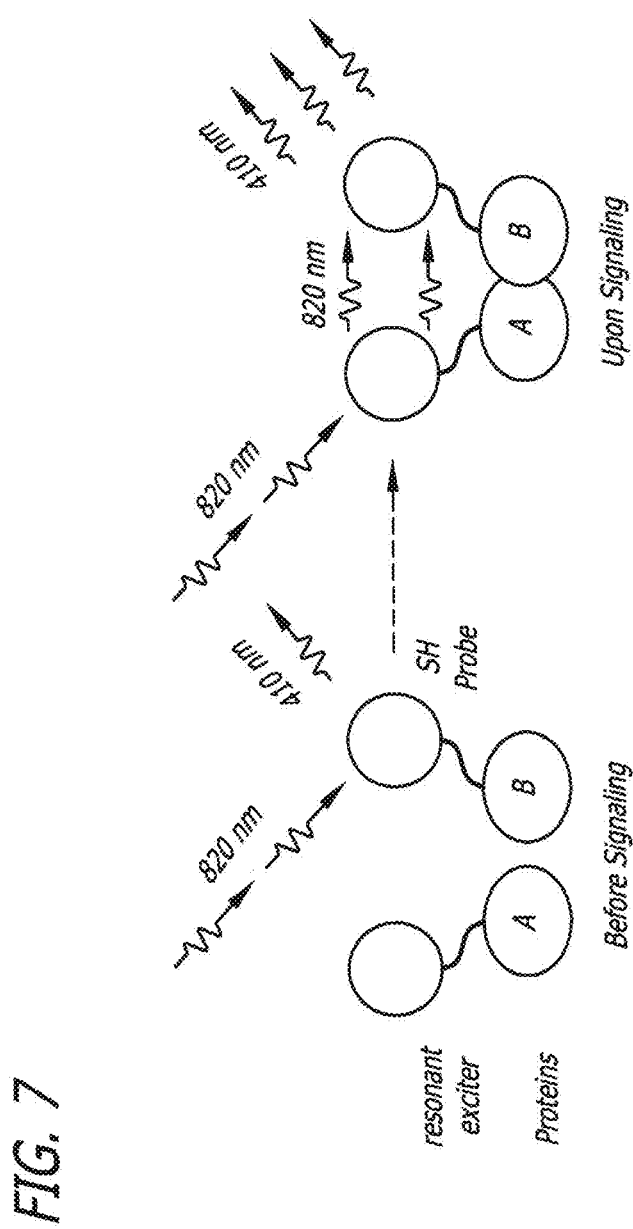
FIG. 7 provides a schematic diagram of the principles of operation of a second exemplary embodiment of the second harmonic generation nanocrystal probe imaging technique in accordance with the current invention.

It should also be understood that although a simple DNA hairpin structure is shown as an example in FIG. 6, the FRESH methodology of the current invention is equally applicable to other biological processes and structures, such as, for example, protein folding or protein-protein interaction. Alternatively, the technique may be used as biosensor to detect any phenomenon of interest. FIG. 7, provides a schematic diagram of the operation of such a sensor, the operation of which will be discussed generically below.

During operation of the SHG probes of the current invention, as shown in FIGS. 6 and 7 above, a continuous wave, modulated or pump energy source, such as a laser emission is focused on a sample of interest. When the exciter nanostructure is energized at the resonance frequency of the energy source, the exciter enhances the electric field within a few nanometers of its vicinity. (See, e.g., Averitt, R. D., Westcott, S. L. & Halas, N. J., J. Opt. Soc. Am. B 16, 1824-1832 (1999), the disclosure of which is incorporated herein by reference.) This enhanced local field couples with neighboring probes when brought within a few nanometers of a probe nanostructure. The coupling of the pump nanostructure with the probe nanostructure enhances the second harmonic emission from the probe nanostructure by orders of magnitude allowing for detection of the second harmonic emission. Similar effects have been demonstrated in Surface Enhanced Raman Spectroscopy (SERS) with an enhancement factor of $10^{14}$. (See, e.g., Nie, S. M. & Emery, S. R., Science 275, 1102-1106 (1997), the disclosure of which is incorporated herein by reference.) The enhanced electric field around the resonant exciter can serve as a ruler of nanometer resolution enabling high resolution imaging. The FRESH technique also allows for the (in vivo/in vitro) imaging of biological processes such as cell signaling, neuroimaging, protein conformation probing, DNA conformation probing, gene transcription, and virus infection and replication in cells in real time.

Example 3

SH Nanoprobe Rapid Detection System

Figure 8:
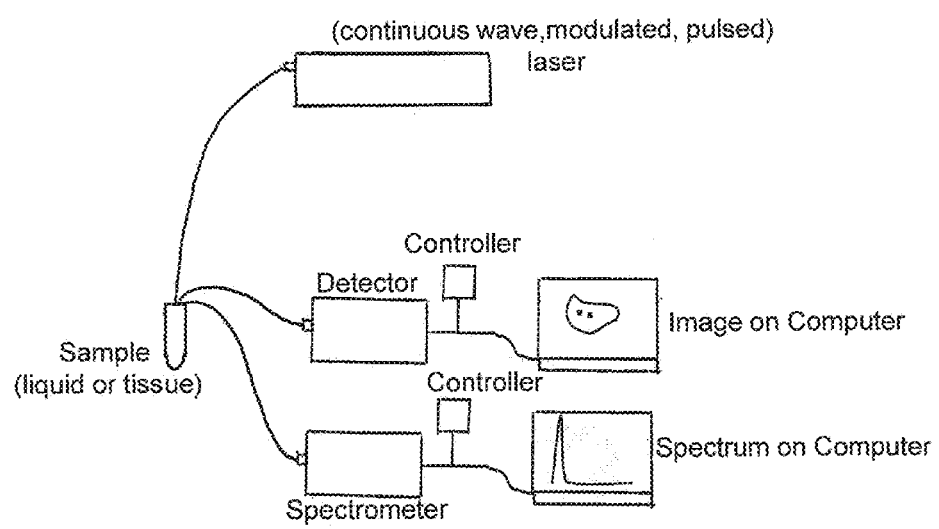
FIG. 8 provides a schematic diagram of the principles of a method of using the SH nanoprobes in a detection scheme, such as, the rapid detection of a specific target, the imaging/detection of medical conditions or neoplasm, and the detection or tracking of a therapeutic agent.

The present invention also relates to the use of SH nanoprobes in rapid detection systems, as shown in FIG. 8, that can be used by primary care level practitioners and field workers in hospitals or doctor's offices in the detection of disorders such as, for example, infectious disease or cancer from liquid or solid sources, among others. Because of the wide applicability of the SH nanoprobes of the current invention, SH nanoprobe detection mixtures can be designed for detection of a variety of conditions, and because of their high sensitivity such detection mixtures require only minimal amounts of SH nanoprobes for each analysis. Indeed, even the presence of a single sign of pathogenesis including, for example, an antigen, peptide sequence, nucleic acid sequence, RNA or DNA of an infectious pathogen could be detected using the rapid detection system of the current invention. As a result, these systems/kits will allow for the detection of a variety of illnesses with portable, inexpensive and easy to use tools, and will allow primary care level and field level workers, such as physicians, nurses, and aid workers to screen and detect a variety of conditions, leading to early detection and more prompt treatment than otherwise possible.

In one exemplary embodiment, such a detection method would include the steps of:
- adding a plurality of SH nanoprobes to the sample;
- waiting for a period of time to allow the SH nanoprobes to bind to the substance in the sample to form an SH nanoprobe-substance mixture;
- removing SH nanoprobes that do not bind to the substance in the sample;
- illuminating the SH nanoprobes-substance mixture in the sample with any conventional excitation source that is compatible with second harmonic generation;
- collecting light returned from the illuminated SH nanoprobe-substance mixture in the sample;
- obtaining an image and/or spectrum of the SH nanoprobe substance mixture in the sample from the collected SH signal; and
- detecting the substance from the image and/or spectrum of the SH nanoprobe-substance mixture.

Although as discussed previously attachment of the SH nanoprobe to the target of interest is not always necessary, in one embodiment of the rapid detection system of the current invention a plurality of optical SH nanoprobes are conjugated with a predetermined chemical compound. The predetermined chemical compound can comprise any target of interest, including, for example a protein, a peptide, a nucleic acid, or an antibody.

As indicated, the sample in such a system may comprise a liquid sample, such as, for example, cerebrospinal fluid, thoracentesis, paracentesis, saliva, urine, semen, mucous, blood, and bronchoalveolar specimen of a living subject, or in another aspect, the sample may comprise a solid sample such as, for example, stool, pap smear, and buccal membrane scrapings of a living subject. In turn, the target of interest may include any substance indicative of pathogenesis including, for example, an antigen, peptide sequence, nucleic acid sequence, RNA or DNA of an infectious pathogen such as, for example, viral, bacterial, parasitic pathogen, or cancer cells. The pathogenesis itself may correspond to any disease compatible with such a detection technique, such as, for example, a disease related to infection, inflammation, or cancer, etc.

The system for detecting a target of interest in a sample includes a plurality of SH nanoprobes, a spectra containing a plurality of spectrum, each spectrum corresponding to a corresponding optical SH nanoprobe-substance mixture, and an optical device for obtaining an image and/or spectrum of an SH nanoprobe-substance mixture in a sample. In operation, a substance is identifiable from comparison the image and/or spectrum of the SH nanoprobes-substance mixture in the sample with the spectra.

As indicated above, the invention comprises the steps of finding a sign of pathogenesis from the image and/or spectrum of the SH nanoprobe-substance mixture in the sample and identifying a corresponding disease from the identified sign of pathogenesis of the plurality of SH nanoprobes with a predetermined chemical compound. Such identification requires first collecting a signal, then obtaining a spectrum or image, and then identifying a sign of pathogenesis. Although any suitable collection of detector, recorder and analyzer may be used to carry out these steps, some exemplary embodiments are described below.

First, with regard to the step of collecting the signal, any suitable detector capable of collecting the SH signal returned from the illuminated SH nanoprobe-substance mixture may be used, such as, for example, an optical spectroscopic system or filter system. Likewise, with regard to the step of obtaining an image and/or spectrum of the illuminated SH nanoprobe-substance mixture from the collected signal, any suitable device capable of recording the signal and obtaining an image or spectrum therefrom may be used. Finally, with regard to the step of identifying the peak of the SH nanoprobe-substance mixture in the spectrum at a predetermined wavelength and using the peak of the SH nanoprobe-substance mixture at the predetermined wavelength as the sign of pathogenesis to identify the disease may be performed, any suitable system, including, for example, an analyzer or data analysis software may be used.

Although not explicitly discussed above as an extension of this detection method, the FRESH technique can also be applied to enhance the SH signal.

Example 4

Imaging/Detecting Medical Conditions or Neoplasm

In another exemplary embodiment, the SH nanoprobes of the current invention may also be used to identify the cause for a medical condition in a living subject. In such an embodiment, the detection method would further include the step of conjugating a plurality of SH nanoprobes with a target responsive to the medical condition, such as, for example, an antibody. Any medical condition compatible with the SH nanoprobes of the current invention may be interrogated in this manner. For example, medical conditions related to infection, inflammation, apoptosis, senescence, etc. may thus be identified.

An effective amount of the SH nanoprobes with the target can be delivered by any suitable means, such as, for example to the circulation system, aerodigestive and genitourinary tracts of the living subject. The SH nanoprobes can then be optically imaged or detected with spectroscopy methods or any other imaging method compatible with the SH signal and the cause of the medical condition can be determined from the images/spectra of the SH nanoprobe with the target. In one alternative embodiment, a plurality of SH nanoprobes displaying distinct emission profiles can be used to identify various medical conditions in parallel.

In another aspect, the present invention can also be used as a method of imaging/detecting a living subject for image guided/navigated surgery. In such a method, an effective amount of SH nanoprobes, conjugated with target molecules responsive to the surgical target itself can be preoperatively delivered to surgical area of interest. For example antibodies responsive to neoplasm can be delivered to tissue(s) associated with the tumor.

Any target compatible with the SH nanoprobes may be imaged using such a system. For example, a neoplasm might comprise a tumor (for example brain tumor, cervical carcinoma) and/or other abnormal tissues. Likewise, the imaging technique may be used with any compatible surgical procedure, such as, for example a biopsy, a surgical excision, a laser ablation, etc. The SH nanoprobes can then be detected in the subject with any conventional excitation source that is compatible with second harmonic generation.

Using such an imaging method, a surgical procedure on the tumor can be guided with the detected SH nanoprobes.

The method can also be used for imaging the SH nanoprobes post-operatively for assessing the performance of the surgical procedure.

Example 5

Detection or Tracking of Therapeutic Agents

Finally, the present invention also relates to a method for detecting the delivery of a therapeutic agent. In such an embodiment, the therapeutic agent would be labeled with an effective amount of SH nanoprobes and delivered to a targeted site of the living subject. The targeted site of the living subject would then be imaged with any conventional excitation source that is compatible with second harmonic generation, and the delivery of the therapeutic agent would be detected from the image of the targeted site of the living subject.

The therapeutic agent can comprise any molecule compatible with the SH nanoprobes of the current invention. For example, in one embodiment a therapeutic cell might be used. In such an embodiment any suitable therapeutic cell might be used including, for example stem cells, package delivery cells carrying a packaged gene or protein, and immunotherapeutic cells. The labeling for a cell would comprise labeling the therapeutic cell by delivering an effective amount of SH nanoprobes to the cell. In another example, the therapeutic agent might comprise a therapeutic gene. In such an embodiment the labeling step would comprise labeling the therapeutic gene by conjugating the SH nanoprobe to the therapeutic gene.

Regardless of the therapeutic agent chosen, the delivery step would comprise delivering the therapeutic agent labeled with the SH nanoprobes by any suitable means, such as, for example intravenous injection.

SUMMARY

While the above description contains many specific embodiments of the invention, these should not be construed as limitations on the scope of the invention, but rather as an example of one embodiment thereof. For example, the SHG probes can be used in conjunction with detection techniques other than the disclosed laser techniques. In addition, the applications of the SHG probes in accordance with embodiments of the invention are not limited to the FRESH dynamic monitoring technique those described above and can be any kind of biological or other imaging applications in which the SHG nanoprobes may be functionally attached to the target molecule(s). Indeed, it is not necessarily even essential that the nanoprobes of the current invention be attached to the molecules of interest. For example, the nanoprobes could be used to perform cell lineage analysis, which can be performed without attaching the crystals to the proteins. Accordingly, the scope of the invention should be determined not by the embodiments illustrated, but by the appended claims and their equivalents.

What is claimed is:

1. A second harmonic generating nanoprobe imager comprising:
    at least one nanocrystal nanoprobe formed of a crystal material being associated with at least one biological target, the crystal material having a unit cell with no inversion symmetry such that the crystal material generates a second harmonic emission when radiated by an external excitation source;
    an external excitation source for radiating the nanocrystal nanoprobe at a frequency such that the crystal material of the nanocrystal nanoprobe generates a second harmonic emission; and
    a detector configured to collect a signal from the second harmonic emission, the signal identifying at least one biological target; and
    wherein the at least one nanocrystal nanoprobe generates the second harmonic emission regardless of the attachment and orientation of the nanocrystal nanoprobe to the at least one biological target.

2. The second harmonic nanoprobe imager of claim 1, wherein the crystal material is selected from the group consisting of organic, inorganic and combinations thereof.

3. The second harmonic nanoprobe imager of claim 2, wherein the crystal material is selected from the group consisting of $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, $Fe(IO_3)_3$, N-(4-nitrophenyl)-(L)-prolinol, urea, 4-Nitroaniline, 2-Methyl-4-nitroaniline, 3-Methyl-4-methoxy-4'-nitrostilbene, $\beta$-$BaB_2O_4$, $LiB_3O_5$, $LiNbO_3$, $KTiOPO4$, $AgGaS_2$, $AgGaSe_2$, $ZnGeP_2$, GaSe, $KH_2PO_4$, $NH_4H_2PO_4$, $KD_2PO_4$, $CsLiB_6O_{10}$, $KTiOAsO_4$, $KNbO_3$, $LiTaO_3$, $RbTiOAsO_4$, $BaTiO_3$, $MgBaF_4$, GaAs, $BiB_3O_6$, $K_2Al_2B_2O_7$, $KBe_2BO_3F_2$, $BaAlBO_3F_2$, $La_2CaB_{10}O_{19}$, $GdCa_4O(BO_3)_3$, $YCa_4O(BO_3)_3$, $Li_2B_4O_7$, $LiRbB_4O_7$, $CdHg(SCN)_4$, $RbTiOPO_4$, $LiInS_2$, $LiInSe_2$, $KB_5O_8 \cdot 4H_2O$, $CsB_3O_5$, $C_4H_7D_{12}N_4PO_7$, a-$HIO_3$, $LiCOOH \cdot H_2O$, $CsH_2AsO_4$, $CsD_2AsO_4$, $RbH_2PO_4$, $CsTiOAsO_4$, $Ba_2NaNb_5O_{15}$, $K_3Li_2Nb_5O_{15}$, $CO(NH_2)_2$, $LiIO_3$, $Ag_3AsS_3$, $HgGa_2S_4$, $CdGeAs_2$, $Ti_3AsSe_3$, CdSe, ZnO, ZnS, ZnSe, ZnTe, CdS, SiC, GaN, and GaSb.

4. The second harmonic nanoprobe imager of claim 1, wherein the nanocrystal nanoprobe is less than or equal to 10 μm.

5. The second harmonic nanoprobe imager of claim 1, wherein the excitation source is selected from the group consisting of continuous wave, modulated and pulsed lasers.

6. A field resonance enhanced second harmonic nanoprobe imager comprising:
    an exciter nanostructure, said exciter nanostructure designed to produce an enhanced local electrical field of a specified frequency when exposed to an excitation source, wherein the exciter nanostructure is attached to a first biological target of interest;
    at least one nanocrystal nanoprobe formed of a crystal material attached to a second biological target of interest, the crystal material having a unit cell with no inversion symmetry such that the crystal material of the nanocrystal nanoprobe generates a second harmonic resonance emission when brought within a resonance range of the resonant electrical field of said exciter nanostructure on said first biological target of interest;
    wherein the first and second biological targets are movable relative to one another such that the exciter nanostructure and at least one nanocrystal may dynamically shift into and out of resonance range;
    an external excitation source for radiating the exciter nanostructure at a frequency such that the exciter nanostructure generates the enhanced electrical field of said specified frequency; and
    a detector configured to collect a signal from the second harmonic emission, the signal identifying when the first and second biological targets are within said resonance range; and
    wherein the at least one nanocrystal nanoprobe generates the second harmonic emission regardless of the attachment and orientation of the nanocrystal nanoprobe to the at least one biological target.

7. The field resonance enhanced second harmonic nanoprobe imager of claim 6, wherein the exciter nanostructure is a metal nanostructure.

8. The field resonance enhanced second harmonic nanoprobe imager of claim 7, wherein the metal nanostructure is a nanostructure selected from the group consisting of nanorods, nanospheres or nanoshells.

9. The field resonance enhanced second harmonic nanoprobe imager of claim 8, wherein the metal nanostructure is made of gold, silver, copper, aluminum, palladium, or platinum.

10. The field resonance enhanced second harmonic nanoprobe imager of claim 6, wherein the crystal material is selected from the group consisting of organic, inorganic and combinations thereof.

11. The field resonance enhanced second harmonic nanoprobe imager of claim 10, wherein the crystal material is selected from the group consisting of $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, $Fe(IO_3)_3$, N-(4-nitrophenyl)-(L)-prolinol, urea, 4-Nitroaniline, 2-Methyl-4-nitroaniline, 3-Methyl-4-methoxy-4'-nitrostilbene, $\beta$-$BaB_2O4$, $LiB_3O_5$, $LiNbO_3$, $KTiOPO4$, $AgGaS_2$, $AgGaSe_2$, $ZnGeP_2$, GaSe, $KH_2PO_4$, $NH_4H_2PO_4$, $KD_2PO_4$, $CsLiB_6O_{10}$, $KTiOAsO_4$, $KNbO_3$, $LiTaO_3$, $RbTiOAsO_4$, $BaTiO_3$, $MgBaF_4$, GaAs, $BiB_3O_6$, $K_2Al_2B_2O_7$, $KBe_2BO_3F_2$, $BaAlBO_3F_2$, $La_2CaB_{10}O_{19}$, $GdCa_4O(BO_3)_3$, $YCa_4O(BO_3)_3$, $Li_2B_4O_7$, $LiRbB_4O_7$, $CdHg(SCN)_4$, $RbTiOPO_4$, $LiInS_2$, $LiInSe_2$, $KB_5O_8 \cdot 4H_2O$, $CsB_3O_5$, $C_4H_7D_{12}N_4PO_7$, a-$HIO_3$, $LiCOOH \cdot H_2O$, $CsH_2AsO_4$, $CsD_2AsO_4$, $RbH_2PO_4$, $CsTiOAsO_4$, $Ba_2NaNb_5O_{15}$, $K_3Li_2Nb_5O_{15}$, $CO(NH_2)_2$, $LiIO_3$, $Ag_3AsS_3$, $HgGa_2S_4$, $CdGeAs_2$, $Ti_3AsSe_3$, CdSe, ZnO, ZnS, ZnSe, ZnTe, CdS, SiC, GaN, and GaSb.

12. The field resonance enhanced second harmonic nanoprobe imager of claim 6, wherein the nanocrystal nanoprobe is less than or equal to 10 μm.

13. The field resonance enhanced second harmonic nanoprobe imager of claim 6, wherein the nanocrystal nanoprobe and the exciter nanostructure are both attached to different spatially separated portions of a single target of interest.

14. The field resonance enhanced second harmonic nanoprobe imager of claim 6, wherein the excitation source is selected from the group consisting of continuous wave, modulated and pulsed lasers.

\* \* \* \* \*

UNITED STATES PATENT AND TRADEMARK OFFICE
CERTIFICATE OF CORRECTION

| | | |
|---|---|---|
| PATENT NO. | : 9,476,830 B2 | Page 1 of 1 |
| APPLICATION NO. | : 11/944264 | |
| DATED | : October 25, 2016 | |
| INVENTOR(S) | : Periklis Pantazis et al. | |

It is certified that error appears in the above-identified patent and that said Letters Patent is hereby corrected as shown below:

IN THE SPECIFICATION

Column 1, lines 17-19, delete "The U.S. Government has certain rights in this invention pursuant to Grant No. HR0011-04-1-0032 awarded by DARPA." and add --This invention was made with government support under Grant No. HR0011-04-1-0032 awarded by DARPA and under Grant No. HD043897 and Grant No. HG004071 awarded by the National Institutes of Health. The government has certain rights in the invention.--

Signed and Sealed this
Twentieth Day of December, 2016

Michelle K. Lee
*Director of the United States Patent and Trademark Office*